United States Patent
Pugliese et al.

(10) Patent No.: US 9,540,631 B1
(45) Date of Patent: Jan. 10, 2017

(54) IMMOBILIZED GLUCOSE OXIDASE FOR USE IN ORAL HYGIENE

(76) Inventors: Peter T. Pugliese, Burnville, PA (US); Steven M. Pugliese, Bernville, PA (US); Joseph A. Ehrhard, Flemington, NJ (US)

( * ) Notice: Subject to any disclaimer, the term of this patent is extended or adjusted under 35 U.S.C. 154(b) by 702 days.

(21) Appl. No.: 12/170,509

(22) Filed: Jul. 10, 2008

Related U.S. Application Data

(63) Continuation of application No. 11/207,414, filed on Aug. 22, 2005, now abandoned.

(60) Provisional application No. 60/609,760, filed on Sep. 14, 2004.

(51) Int. Cl.
| | | |
|---|---|---|
| A61Q 11/00 | (2006.01) | |
| C12N 11/16 | (2006.01) | |
| A61K 8/66 | (2006.01) | |
| A61K 6/00 | (2006.01) | |
| A61K 9/51 | (2006.01) | |
| C12N 11/14 | (2006.01) | |

(52) U.S. Cl.
CPC ............. *C12N 11/16* (2013.01); *A61K 6/00* (2013.01); *A61K 8/66* (2013.01); *A61K 9/5115* (2013.01); *A61Q 11/00* (2013.01); *C12N 11/14* (2013.01)

(58) Field of Classification Search
None
See application file for complete search history.

(56) References Cited

U.S. PATENT DOCUMENTS

| | | | | |
|---|---|---|---|---|
| 3,841,971 | A * | 10/1974 | Messing | 435/175 |
| 3,902,970 | A * | 9/1975 | Levin | G01N 27/3271 204/403.11 |
| 4,102,746 | A | 7/1978 | Goldberg | 435/96 |
| 4,150,113 | A | 4/1979 | Hoogendoorn et al. | |
| 4,178,362 | A | 12/1979 | Hoogendoorn et al. | |
| 4,240,438 | A * | 12/1980 | Updike et al. | 600/347 |
| 4,269,822 | A | 5/1981 | Pellico et al. | |
| 4,307,195 | A * | 12/1981 | Karasawa et al. | 204/403.1 |
| 4,425,434 | A | 1/1984 | Rosevear | 435/176 |
| 4,564,519 | A | 1/1986 | Pellico et al. | |
| 4,578,265 | A | 3/1986 | Pellico et al. | |
| 4,713,333 | A | 12/1987 | Chiang et al. | 435/96 |
| 5,741,659 | A * | 4/1998 | Ralls et al. | 435/23 |
| 5,780,260 | A | 7/1998 | Wedekind et al. | 435/43 |
| 5,846,430 | A * | 12/1998 | Cockett et al. | 210/691 |
| 6,114,337 | A | 9/2000 | Pugliese et al. | |
| 6,221,341 | B1 | 4/2001 | Montgomery | 424/53 |
| 6,309,656 | B1 | 10/2001 | Pugliese et al. | |
| 6,448,251 | B1 | 9/2002 | Pugliese et al. | |
| 6,497,892 | B2 | 12/2002 | Pugliese et al. | |
| 2004/0013658 | A1 * | 1/2004 | Fulton et al. | 424/94.1 |

FOREIGN PATENT DOCUMENTS

WO      WO 9723241 A1 *   7/1997

OTHER PUBLICATIONS

Milagres et al. Electroanalysis (1996) 8(5): 489-493.*
Definition of "steady state" downloaded from http://merriam-webster.com/dictionary/steady%20state on May 9, 2016.*
Defintion of "adsorbed" downloaded from http://www.thefreedictionary.com/adsorbed on May 16, 2016.*
Definition of "sequester" downloaded from http://www.dictionary.com/browse/sequester on May 9, 2016.*
Bentley, Ronald, "Glucose Oxide", The Enzymes, Second Edition, (1963) p. 567-586, Academic Press, New York and London.
Weibel, Michael K. et al., "Insolubilized Enzymes, Kinetic Behavior of Glucose Oxidase Bound to Porous Glass Particles", Biochem (1971)124, 801-807, Great Britain.
Soder, "Proteolytic Activity in the Oral Cavity: Proteolytic Enzymes from Human Saliva and Dental Plaque Material", J. Dent Res Supplement, (1972)vol. 51, No. 2, p. 389-393, Stockholm, Sweden.
Helmerhorst, Eva J., "Whole Saliva Proteolysis, Wealth of Information for Diagnostic Exploitation", Annals of N.Y.Academy of Science, (2007)1098, p. 454-460.
Pye, Kendall E. et al., "Investigation of the Physical Properties of Immobilized Enzymes", Methods in Enzymeology: Immobilized Enzymes, (1976) vol. 44, p. 357-372, Academic Press, Orlando, Florida.
Gibson, Quentin H. et al., "Kinetics and Mechanism of Action of Glucose Oxidase", The Journal of Biological Chemistry, (1964) vol. 239, No. 11, p. 3927-3934, U.S.A.
Jones, Julian R. et al., "Hierarchical Porous Materials for Tissue Engineering", Philosophical Transactions of The Royal Society, (2006)vol. 364, p. 263-281.
Grochulski, Pawel et al., "Two Conformational States of Candida Rugosa Lipase", Protein Science (1994) vol. 3, p. 82-91. Cambridge University Press, U.S.A.

(Continued)

*Primary Examiner* — Susan Hanley
(74) *Attorney, Agent, or Firm* — Lori J. Sandman, Esq.; Sandman Law Office, PLLC

(57) ABSTRACT

Compositions are provided to immobilize and protect oxidase enzymes from proteolytic and hydrolytic attack, utilizing a porous, inert organic, or inorganic, substrate matrix useful in generating hydrogen peroxide in situ for use in oral, topical mucosal and intracavity uses for use in or on the human body and other mammalian, reptile, fish and amphibians.

The selected porosity of the support matrix provides the basis for generating hydrogen peroxide on a steady state basis. Both diatomaceous earth and silica gel, either in natural or pre-silanized forms, allow for the excluding of non-preferred enzymes from the support matrix, and for diffusion of the peroxide in the reduction of oral pathogens and their attendant malodorous compounds, or other pathogens in the mucosa, bodily fluids and cavities, in addition to oxidizing color bodies to affect bleaching.

6 Claims, No Drawings

(56) References Cited

OTHER PUBLICATIONS

Schmitt, Jutta et al., "Blocking the Tunnel: Engineering of Candida Rugosa Lipase Mutants with Short Chain Length Specificity", Protein Engineering (2002)vol. 15, No. 7, p. 595-601, Oxford University Press.

Marsh, P.D., "Microbiological Aspects of the Chemical Control of Plaque and Gingivitis", J Dent Res, (1992) 71, (7) p. 1431-1438.
Tzanov et al., Journal of Biotechnology, 2002, vol. 93, pp. 87-94.
Soares et al. Biotechnology Progress, 2003, vol. 19, pp. 803-807.

* cited by examiner

IMMOBILIZED GLUCOSE OXIDASE FOR USE IN ORAL HYGIENE

CROSS-REFERENCE TO OTHER APPLICATIONS

This application is a continuation of U.S. application Ser. No. 11/207,414, filed Aug. 22, 2005, now abandoned, which in turn claims priority from U.S. Provisional Application No. 60/609,760, filed Sep. 14, 2004.

BACKGROUND OF THE INVENTION

Hydrogen Peroxide

Hydrogen peroxide, or H2O2, is naturally found in human cells and is used for disinfection. Hydrogen peroxide has anti-fungal, anti-bacterial, anti-parasitic and anti-viral activity. Once hydrogen peroxide interacts with certain enzymes, catalase or peroxidase, it yields water and an oxygen ion. Two singlet oxygen ions make stable oxygen, O2.

The bacterial origin of dental disease is well established. Dental caries, gingivitis and halitosis are all associated with resident oral bacteria. Reduction in their number by germicidal agents is a current aim to control these oral conditions. Glucose oxidase, a flavo-enzyme (GLU-OXY), is known to act upon a glucose substrate to produce hydrogen peroxide and gluconic acid. Since the mouth also contains highly active proteases, any additional oxidase enzyme can be rapidly inactivated by proteolytic action of these protease enzymes.

Glucose oxidase (B-D-glucose: oxygen I-oxidoreductase. ECI.1.3.4.) flavoenzyme is widely used for the determination of glucose in body fluids, and in removing residual glucose and oxygen from beverages and foodstuffs. See William. D. C., or al Clin. Chem. 22, 372, 1976. Furthermore, glucose oxidase-producing molds, such as *Aspergillus* and *Penicillium* species, have been used for the biological production of gluconic acid, as well as the oxidase. A unit is defined as the enzyme amount which causes oxidation of one micromole of glucose per minute at 25 C and pH 7.0. Glucose oxidase combined with an appropriate cofactor catalyses the oxidation of R-D-glucose to D-glucono-1, 5-lactone and hydrogen peroxide, using molecular oxygen as the electron acceptor. The pH range is from 4 to 7, with an optimum pH at 5.5. The enzyme, GLU-OXY, is a dimeric holoprotein with a molecular weight of 160 (KDA 160.000 Daltons), containing one tightly bound (Kw 1×10-10) flavin adenine dinueleotide (FAD) per monomer, as cofactor. The FAD is not covalently bound and so can be released from the holoprotein following denaturation.

The human oral cavity° is known to contain other highly active proteolytic enzymes, known as proteases, and concurrently, the afore-described glucose oxidase. The latter is useful to act upon glucose to produce gluconic acid and hydrogen peroxide. The peroxide, in turn, is known to be converted by oral catalase to oxygen and water. The liberated oxygen has a germicidal effect upon the oral cavity. If the oral GLU-OXY concentration is increased, for example, by addition to a dentifrice, the proteolytic enzymes will interfere with enhanced level of glucose oxidase enzyme, by destroying the glucose oxidase. So, there is a need to protect glucose oxidase from the ever present oral proteolytic enzymes. The same utility of Glucose Oxidase can be found in the mucosa, in open wounds and within other body cavities such as the vagina, the nasal and auditory canal, the urethra and induced opening such as venous punctures.

Proteolytic enzymes are large group of natural proteins (polypeptides) with a peptide chain coiled to form an alpha-helix, and which display enzymatic activity; that is, they catalyze specific organic, or even inorganic, reactions. A typical proteolytic protein-splitting enzyme is alpha-chymotrypsin of a molecular weight c.25,000. It has a quite general power of affecting the hydrolysis of carboxyl derivatives, amides, esters, and hydrazides.

Attempts to exploit these natural antimicrobial systems have been directed to both the oral care field and the gastrointestinal tract. U.S. Pat. No. 4,150,113 and U.S. Pat. No. 4,178,362 (Hoogendom, et al) describe dentifrice compositions containing glucose oxidase, that react with plaque and salivary glucose to produce low levels of hydrogen peroxide. Hydrogen peroxide production by such systems is however, highly irregular, due to the non-uniform distribution and unpredictable availability of substrate, namely glucose, in the oral cavity, and instability of the enzyme in the presence of proteases. The effects are described as transient due to the inherent instability of the glucose Oxidase enzyme.

U.S. Pat. No. 4,269,822. U.S. Pat. No. 4,564,519, and U.S. Pat. No. 4,578,265 (Pellico, etal) further describe dentifrice compositions containing an oxido-reductase enzyme and its specific substrate in an aqueous solution for the purpose of producing in the oral cavity hydrogen peroxide or other antimicrobial oxidizing compounds such as hypothiocyanite ion. A more predictable amount of hydrogen peroxide (and subsequently hypothiocyanite ions) is produced by the compositions of Pellico et al, compared with those of the Hoogendorn references (U.S. Pat. Nos. 4,150,113 and 4,178,362). The differences between the two compositions reflect the availability of glucose in the oral cavity as substrate for glucose oxidase.

U.S. Pat. No. 4,564,519 describes a chewable dentifrice, such as a chewing gum or lozenge, which contains a dual enzymes system for producing hypothiocyanite ions upon being chewed or otherwise activated by the moisture in saliva. Such compositions stiffer from similar drawbacks to those mentioned immediately above, namely a slow rate of enzymatically-produced hydrogen peroxidase as well as a reliance on a cariogenic compound.

The formation of calculus and dental plaque is the primary source of gingivitis, dental caries, periodontal disease, tooth staining and tooth loss.

Dental calculus, or tartar as it is sometimes called, is a deposit, which forms on the surfaces of the teeth at the gingival margin. Mature calculus consists of an inorganic portion which is largely calcium phosphate arranged in a by hydroxyapatite crystal lattice structure similar to bone, enamel and dentine. An organic portion is also present and consists of desquamated epithelial cells, leukocytes, salivary sediment, food debris and other various types, unless stained or discolored by some extraneous agent. In addition to being unsightly and undesirable from an aesthetic standpoint, the mature calculus deposits are constant sources of irritation of the gingiva, Plaque can be defined as a complex microbial community, with bacteria comprising approximately 70-80% of the plaque matrix. It has been estimated that as many as 400 distinct bacterial species may be found in plaque. This mix includes both aerobic and anaerobic bacteria, fungi, and protozoa. Viruses have also been found in samples of dental plaque. In addition to the bacterial cells, plaque contains a small number of epithelial cells, leukocytes, and macrophages. The cells are contained within an extra cellular matrix, which is formed from bacterial products and saliva.

The extra cellular matrix contains protein, polysaccharide and lipids. This matrix of organisms and oral exudates continues expanding and coalesces with other plaque growths situated nearby. The bacteria synthesize levans and glucans from sucrose found in the oral cavity providing energy for the microorganisms. These glucans, levans, and microorganisms form an adhesive skeleton for the continued proliferation of plaque.

Retarding and/or stopping the proliferation of plaque and calculus are critical to maintaining good oral health. Plaque and calculus formation may lead to dental caries, gingival inflammation, periodontal disease, and ultimately tooth loss. Additionally, calculus and plaque along with behavioral and environmental factors lead to formation of dental stains, significantly affecting the aesthetic appearance of teeth. Behavioral and environmental factors that contribute to teeth staining propensity include regular use of coffee, tea, wine, cola or tobacco products.

Plaque has been classified by association with disease state as "health-associated" or "disease associated". The latter classification is related to differences in the microbial composition of dental plaque in health versus disease. A newly cleaned tooth surface is rapidly covered with a glycoprotein deposit referred to as "pellicle". The pellicle is derived from salivary constituents which are selectively adsorbed onto the tooth surface. The formation of pellicle is the first step in plaque formation.

The pellicle-coated tooth surface is colonized by Gram-positive bacteria such as *Streptococcus sanguts, Streptococcus mutans*, and *Aetinornyces viscosus*. These organisms are examples of the "primary colonizers" of dental plaque. Bacterial surface molecules interact with components of the dental pellicle to enable the bacteria to attach or adhere to the pellicle-coated tooth surface. Within a short time after cleaning a tooth, these Gram-positive species may be found on the tooth surface. After the initial colonization of the tooth surface, plaque increases by two distinct mechanisms: 1) the multiplication of bacteria already attached to the tooth surface, and 2) the subsequent attachment and multiplication of new bacterial species to cells of bacteria already present in the plaque mass. These new bacteria include anaerobic Grain-negative species such as *Fusobacterium nucleatum* and *Prevotella intetnzedia*; and the *Capnocytophaga* species. The overall pattern observed in dental plaque development is a very characteristic shift from the early predominance of Grain-positive facultative microorganisms to the later predominance of Gram-negative anaerobic microorganisms, as the plaque mass accumulates and matures. This developmental progression is also reflected in the shifts in predominant microorganisms that are observed in the transition from health to disease. Studies of plaque taken from sites of health or disease and examined either microscopically or by culturing have demonstrated distinct differences in health versus disease-associated microbial populations.

Halitosis has also been an unsolved physiological problem for centuries, and remains as such in the modern era. Halitosis is the technical term for bad breath, a condition estimated to affect 50 to 65% of the population. Up to 90% of cases are thought to originate from sources in the mouth, including poor oral hygiene, periodontal disease, coating on the tongue, impacted food, faulty dental restoration, and throat infection. The chemical basis of halitosis lies in the concentration of mouth-bound volatile and odiferous compounds, primarily organic and inorganic sulfides as well as organic amines. These odiferous volatiles are biologically synthesized by particular microorganisms that reside in the oral cavity. Halitosis is primarily caused by certain anaerobic strains of bacteria (Rosemberg, M., Bad Breath: Research Perspectives. Rumor Publishing, 1995). Specifically, the proliferation in saliva of the anaerobic bacterial pathogen *Fusobacterium* Species, in combination with other anaerobes, has been shown as the major biological source of halitosis.

Factors that support the growth of these bacteria will predispose a person to halitosis. Examples include accumulation of food within pockets around the teeth, among the bumps at the back of the tongue, or in small pockets in the tonsils; sloughed cells from the mouth; and diminished saliva flow. Mucus in the throat or sinuses can also serve as a breeding ground for bacteria. Conditions are most favorable for odor production during the night and between meals.

Although bad breath primarily represents a source of embarrassment or annoyance, research has shown that the sulfur gases most responsible for halitosis (hydrogen sulfide and methyl mercaptan) are also potentially damaging to the tissues in the mouth, and can lead to periodontal disease (a bacterial infection of the gains and ligaments supporting the teeth). As periodontal disease progresses, so may the halitosis, as bacteria accumulate in the pockets that form next to the teeth.

The ultimate oral cleaning level is what dentists provide during prophylaxis; daily oral care at home requires products with multiple ingredients working by different mechanisms to provide satisfactory cleaning and whitening, Oral care products for daily use such as dentifrice and rinses provide overall cleaning, but it is necessary to add ingredients for provision of anti-plaque and anti calculus benefits as well as breath freshening, stain removal, stain control and tooth whitening. Such ingredients for removal and control of stain and for whitening include bleaches, abrasives or chemical chelants. Bleaches added to dentifrices are typically present in low concentrations due to stability and safety limits unique to toothpastes. At these low concentrations bleaches, typically oxidizing agents, are generally ineffective at tooth whitening and stain control. Dental abrasives provide whitening benefits on 'brushed' areas of teeth, but unfortunately are of limited effect in controlling aesthetically undesirable stains that Joint along the gumline and interproximally.

Although products containing chemical oxidizing agents and other plaque and calculus reduction agents are known, there is a continuing need to develop improved products, in particular products that provide enhanced overall cleaning by concurrently attacking the calculus, plaque, and staining problems.

Attempts to exploit these natural antimicrobial systems have been directed to both the oral care field and the gastrointestinal tract. U.S. Pat. No. 4,150,113 and U.S. Pat. No. 4,178,362 (Hoogendom, et al) describe dentifrice compositions containing glucose oxidase, that react with plaque and salivary glucose to produce low levels of hydrogen peroxide. Hydrogen peroxide production by such systems is, however, highly irregular, due to the non-uniform distribution and unpredictable availability of substrate, namely glucose in the oral cavity and instability of the enzyme in the presence of protease.

U.S. Pat. No. 4,269,822, U.S. Pat. No. 4,564,519, and U.S. Pat. No. 4,578,265 (Pellico, et at) further describe dentifrice compositions containing an oxidoreductase enzyme and its specific substrate in an aqueous solution for the purpose of producing in the oral cavity hydrogen peroxide or other antimicrobial oxidizing compounds such as hypothiocyanite ion. A more predictable amount of hydrogen peroxide (and subsequently hypothiocyanite ions) is produced by the compositions of Pellico et al, compared with those of the Hoogendom references (U.S. Pat. Nos. 4,150,113 and 4,178,362). The differences between the two compositions reflect the availability of glucose in the oral cavity as substrate for glucose oxidase.

U.S. Pat. No. 4,564,519 describes a chewable dentifrice, such as a chewing gum or lozenge, which contains a dual enzymes system for producing hypothiocyanite ions upon being chewed or otherwise activated by the moisture in saliva. Such compositions suffer from similar drawbacks to those mentioned immediately above, namely, a slow rate of enzymatically-produced hydrogen peroxide as well as a reliance on a cariogenic compound.

Background Oral Proteases

The oral cavity contains many specific and non-specific proteases, both endogenous and exogenous. Exogenous types are from both viral and bacterial sources, while endogenous protease are mainly secreted by salivary glands. Some of these proteases include: three enzymes including leucine amino peptidase, dipeptidyl peptidase IV and trypsin-like proteinase, salivary matrix metalloproteinases (MMPs) (may participate in the pathogenesis of mucosal lesions and dentinal caries), particularly activity of MMP-(collagenase-2) and MMP-9 (gelatinase B), cysteine peptidases, aminopeptidase, neuropeptide-degrading enzymes and secreted aspartic proteases (Saps) These enzymes destroy a wide variety of proteins, including other enzymes.

Degradation of Glucose Oxidase by Salivary Proteases

Glucose oxidase in the presence of glucose and oxygen will convert glucose to hydrogen peroxide and gluconic acid at a fast rate, (GOx from *Aspergillus nigec* Michaelis constant KM 33 The Michaelis constant Kin is defined as the substrate concentration at ½ the maximum velocity) By measuring the oxygen consumption the reaction rate can be followed by using a Clark oxygen electrode. Three test cells were set up containing five milligrams of the enzyme in 10 ml of saline at pH 7.0. Test cell one contained only saline and enzyme, cell two contained enzyme plus five milligrams of commercial bacterial protease from *Bacillus polymyra* (1 unit/milligram), and cell three contained glucose oxidase enzyme plus two milliliter of human saliva. The cells were incubated qt 37 degrees Centigrade for 10 minutes. Two hundred millimoles of glucose were then added to each cell and the oxygen consumption measured over five minutes.

Results

Cell one showed 52% of the oxygen consumed in 5 minutes, cell two showed 10% of the oxygen consumed in five minutes and cell three showed 8% of the oxygen consumed in five minutes. These results confirmed the degradation of glucose oxidase by oral proteases.

Immobilized Glucose Oxidase Protection from Salivary Protease

Immobilization of enzymes is an established procedure in biochemistry, many factors affect the choice of substrate on which to fix the enzyme, it is often convenient to immobilize the enzyme on a support material by adsorption, deposition or a chemical means. Useful supports are porous glass, celite, porous hydrophobic resins and ion exchange materials. Depending on the properties of the support (particle size, pore size, etc) and other parameters, the enzyme loading is variable. In addition the solvent can affect the enzyme catalyzed reaction by influencing the solvation of the substrates and products or by direct interaction with the enzyme. Water is the main solvent in saliva.

Effects of the Water Content

Even in biocatalytic systems which contain mainly organic solvent and/or organic substrates, the catalytic activity is highly dependent on the amount of water present. The amount of water is best quantified in terms of water activity since the water activity is correlated with the hydration of the enzyme which in turn governs the catalytic activity. *Salvia* is 90+% water, so we can consider the solvent system as water.

SUMMARY OF THE INVENTION

According to the present invention, means are provided to immobilize and protect oxidase enzyme compositions from proteolytic and hydrolytic attack, utilizing a porous, inert, inorganic or organic, support matrix useful in generating hydrogen peroxide in situ on a steady state basis, in the presence of a suitable available, reactant substrate. The enzyme is physically immobilized within the pores of the support matrix. The porosity of the support matrix selectively excludes bulkier, non-preferred enzymes and other non-preferred inhibitory reactants, but allows for the transport of reactant substrate through the support matrix and the diffusion of hydrogen peroxide from the support matrix. The result is a useful means of generating hydrogen peroxide continuously on a steady state basis in the presence of the reactant substrate, that has utility in the reduction or elimination of microbes, localized superoxygenation, bleaching of certain tissues, and reduction of odors due to oxidation of malodorous compounds and the reduction or elimination of microbes that cause malodors and disease.

According to the invention, there is provided a composition and method in which is an immobilized enzyme composition has been stabilized from proteolytic and hydrolytic attack while useful in generating hydrogen peroxide with in situ of an oral cavity on a steady state basis in the presence of a suitable reactant substrate, including an oxidase enzyme able to generate hydrogen peroxide in the oral cavity, in the mucosa, and in other body cavities and surfaces while the enzyme is adsorbed onto a 3-dimensional selective organic or inorganic support matrix, with the matrix having a porosity that selectively excludes both bulkier, non-preferred enzymes and other inhibitory reactants, but allows for transport of the reactant substrate through the support matrix and for the diffusion on a steady state basis of hydrogen peroxide from the support matrix.

Further according to the invention, there is provided a method of using these compositions for the reduction of infections such as gingivitis, plague, toxic shock, hoof rot, hairy hoof wart, mastitis, acne, infected wounds, urinary tract infections and other bacterial/yeast/mold/viral infections via the sustained in situ generation of hydrogen peroxide.

Also, according to the invention, there is provided a composition useful for the reduction of a mammalian infection from a list selected from the group consisting of a dentifrice (toothpaste/powder), dental floss, dental solutions, including irrigation fluids, whitening tooth gel, candy, gum, breath strip, lozenge, gel cap, substrate whitening strip, oral rinse/spray, lipstick, lip gloss, lip balm, toothpick, teat sealants, and barrier dips to prevent mastitis in mammalians, tooth cloths/brushes, creams, ointments, irrigation solutions (oral, vaginal, anal, ocular, ear, nasal, wound); medical devises coated with the composition, including but not limited to wound management devises including but not limited to hydrogels, hydro colloids, dressings, urinary catheters, venous catheters, stents, shunts, NG tubes, feeding tubes, airway management devises, ear and wound drains, sutures, tampons, feminine hygiene pads, diapers, urine and fecal collection devises, and other such devises where bacterial contamination or colonization is undesirable.

DETAILED DESCRIPTION OF THE INVENTION

While the specification concludes with claims, which particularly point out and distinctly claim the invention, it is believed the present invention will be better understood from the following description.

All documents cited are incorporated herein by reference; the citation of any document is not to be construed as an admission that it is prior art with respect to the present invention. Herein, "comprising" means that other steps and other ingredients which do not affect the end result can be added. This term encompasses the terms "consisting of" and "consisting essentially of".

By "oral composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral composition of the present invention may be in the form of a toothpaste, dentifrice, tooth powder, topical oral gel or film, mouth rinse, floss, denture product, mouth spray, lozenge, oral tablet, or chewing gum.

The term "dentifrice", as used herein, means paste, gel, or liquid formulations unless otherwise specified. The dentifrice composition may be a single phase composition or may be a combination of two or more dentifrice compositions. The dentifrice composition may be in any desired form, such as deep striped, surface striped, multilayered, having the gel surrounding the paste, or any combination thereof. Each dentifrice composition in a dentifrice comprising two or more separate dentifrice compositions may be contained in a physically separated compartment of a dispenser and dispensed side-by-side, The term "dispenser", as used herein, means any pump, tube, or container suitable for dispensing toothpaste.

The term "orally acceptable carrier" as used herein means any safe and effective materials for use in the compositions of the present invention. Such materials include fluoride ion sources, additional anti-calculus agents, buffers, anti-microbials, abrasive polishing materials, alkali metal bicarbonate salts, thickening materials, humectants, water, surfactants, titanium dioxide, flavor system, sweetening agents, coloring agents, and mixtures thereof.

The present invention provides oral compositions that provide enhanced overall cleaning and whitening of and stain removal from teeth, the compositions comprising as an essential ingredient one or more immobilized enzymes capable of converting simple and/or complex sugars into peroxides or neutral materials. In particular, the preferred enzyme will be Glucose Oxidase immobilized with a spherical silica substrate of specific pore size.

Other potential enzymes include, but are not limited to. lactoperoxidase, dextranase and mutanase.

Other potential substrates include, but are not limited to diatomaceous earth, and cyclodextritins.

Without wishing to be limited to a particular mechanism of action, it is believed that the superior breath freshening, stain removal and prevention benefits of the present immobilized peroxide producing enzymes are derived at least in part from their ability to convert sugar to peroxide at a steady-state rate while remaining in the mouth for extended periods of time.

The oral composition of the present invention may be in the form of a dentifrice, toothpaste, tooth powder, topical oral gel, mouth rinse, denture product, mouth spray, lozenge, oral tablet, oral wafer, oral film/strip, or chewing gum.

The present compositions will optimally have a pH ranging from about 4.0 to about 10.0 Preferred pH of the compositions is from about 5.0 to about 9.0.

In addition to the components described above, the present compositions may comprise additional components, which are described in the following paragraphs. The present invention also relates to methods for cleaning and polishing teeth and reducing the incidence of stain, plaque, gingivitis and calculus on dental enamel, and for controlling or eliminating bad breath.

The method of use herein comprises treating a subject's dental enamel surfaces and oral mucosa with the oral compositions according to the present invention. The method of use may be by brushing with a dentifrice, rinsing with a mouth rinse or chewing a gum product. Other methods include contacting the topical oral gel, mouth spray, or other form with the subject's teeth and oral mucosa. The subject may be any person, or lower animal, whose tooth surface contacts the oral composition.

It should be understood that the present invention relates not only to methods for delivering the present compositions to the oral cavity of a human, but also to methods of delivering these compositions to the oral cavity, other body cavities and certain mucosal and topical surfaces of the body of other animals, e.g., household pets or other domestic animals, or animals kept in captivity in addition to humans.

The method of use herein also comprises other parts of mammalians wherein the in-situ generation of hydrogen peroxide in the presence of glucose in steady state fashion may have utility in the prevention of disease or infection, such as topical use for acne, wound care to prevent infection, as an adjunct to a medical device coating to prevent infection in the blood steam, mucosa, or other body cavities.

General Properties of Glucose Oxidase Produced from *Aspergillus Niger* Strain of Microorganism A suitable strain of *A. niger*-based GLU-OXY is supplied as freeze-dried powder from Calzyme Laboratories, Inc. of California, as Catalog #077A0250. It is a flavin-containing glycoprotein, with 20% (w/w) of the molecule as carbohydrate (FAD). A holoprotein contains a cofactor, such as FAD or FADHI combined with the major protein, called the apoprotein.

The holoprotein is made up of two identical subunits of Mol. W circa 80,000 D. The monomers are connected non-covalently via a long but narrow contact area. There are 120 contact points between the dimers centered around 11 residues which form dither salt linkages or hydrogen bonds. The monomeric molecule is a compact spheroid with approximate dimensions, 60 A×52 A×37 A. The monomer folds into two structural domains (see below). One of the domains binds FAD, and the other is involved with substrate binding. The corresponding dimensions of the dimer are 70 A×55 A×80 A. The diffusion coefficient of the holoenzyme in 0.1M NaCl is $4.94 \times 10^{-1}$ cm$^2$·s'.

Availability of Microorganism for Production of GLU-OXY Enzyme

Source: *Aspergillus niger*

Form: Freeze-dried powder

Solubility: Soluble in water and dilute buffer

Stability: Stable when stored at −20 degrees C.

Activity: 200-250 U/mg
Protein: 90-95%
Catalog No.: 077AO250 (Calzyme Labs, Inc.)
GLU-OXY, purified is also available from Worthington Labs, as a dialyzed lyophilized powder.
Store at 2-8 degrees C. Code: GOP.
Reagents for Conducting Glucose Conversion by GLU-OXY Enzyme in an Assay
1. 0.1 M Potassium phosphate buffer, pH 7.0
2. 1% O-Dianisidine in distilled water.
3. Dianisidine-buffer mixture; prepared by mixing 1.0 ml of O-Dianisidine (10 mg/ml) with 100 mg of 0.1 M phosphate buffer, pH 7.0. The solution is then oxygenated for five minutes.
4. 10% D-Glucose in distilled water. Allow mutarotation to come to equilibrium by standing overnight
5. Peroxidase (1 mg/ml) in distilled water.
6. Glucose oxidase (test enzyme) solution prepared in 0.1 M phosphate buffer, pH 7.0 to yield a final concentration of 0.15 U/ml.

Procedure
1. Set spectrophotometer (equipped with a strip chart recorder and temperature control) at 436 nm and 25 degrees C.
2. Into a cuvette place the following reagents:
   Dianisinde—buffer mixture (oxygenated) 2.5 ml
   10% D-Glucose 0.3 ml
   Peroxidase 0.1 ml
   Incubate in spectrophotometer at 25 degrees C. for 3-5 minutes to achieve temperature equilibration.
3. Establish bank rate, if any, at 436 mm.
4. Initiate the reaction by adding 0.1 ml of glucose oxidase (enzyme) solution. Record the increase in absorbance at 436 nm for 4-6 minutes.
5. Calculate the Delta E 436 nm/minute.

Immobilization of the Enzyme by Adsorption on Controlled Pore Size Materials

The purpose of immobilization is to protect the enzymes from protease over a period of tine, and to protect the glucose oxidase from the attack by other enzymes present in the mouth. The materials for glucose oxidase immobilization have to be acid washed (to ensure very low amounts of cations, like iron, calcium, and others, that can inactivate the enzyme by the formation of chelates).

The pore size of the material should be at least twice the dimensions of the enzymes molecule. For the enzyme, obtained from *Aspergillus* species, the diameter is about 84 angstroms; so the pore size should be at least 168 angstroms. A too small pore size material will prevent the enzyme from entering the material pores, thus exposing the enzyme to degradation by oral proteases. The best activity and stability of immobilized glucose oxidase was obtained using a matrix with a pore size between 300-350 angstroms.

In order to obtain a high loading of enzyme in the pores, the process should follow these steps:

(a) Preconditioning the carrier: Its purpose is to ensure the best conditions of the adsorption of the enzyme at the optimum conditions for the activity (pH=5.6). Then the material is thoroughly rinsed with deionized water, because the buffer molecules will occupy some of the active sites for adsorption.

(b) Immobilization: The material should be exposed to an excessive quantity of enzyme, at the optimum temperature, for a short time (2-3 hours), then the enzyme immobilization will continue at room temperature for a longer time (15 hours).

(c) Rinsing and drying: After the immobilization is finished, the material is washed with sodium chloride solution, then with buffer, and finally with deionized water. The material can be air dried, or in a convection oven, with temperature not exceeding 45° C.

There are several techniques that can be used for the immobilization process.

The in-column procedure can be conducted in two ways: in a plug-flow method, the material is loaded in the column with a heating jacket and the NaCl and/or enzyme solutions travel through the material by gravity. Another method is the fluidized bed, where the solutions travel against the gravity, using pumps, and the flow rate can be adjusted so the particles are in continuous motion. Another procedure is using a mixing or shaking bath.

A suitable particulate material is diatomaceous earth (DIE), a soft bulky, solid material percent 88% silica, composed of the skeletons of prehistoric aquatic plants related to algae (diatoms) with a 3-dimensional framework. They are generally insoluble in acids and DIE absorbs several times its weight in water. Silanes are liquid compounds of silicon and hydrogen of the formula, $SnHn+2$, being analogous to organic alkanes, like methane and ethane. Organo-functional silanes are known for their ability to bond organic polymer systems, like poly peptides, to inorganic substrates. It is known that by first silanizing the DIE substrate, and then coupling the GLU-OXY enzyme with glutaraldehyde to the S102 bonds already generate on the DIE by the prior silanization, a useful formula results.

The resulting bonded glucose oxidase on DIE has a tan appearance. Our experiments have shown that the thusly immobilized GLU-OXY enzyme is protected from the highly active oral proteases. This permits the GLU-OXY enzyme to continue to convert oral glucose to the lactone, and to orally useful hydrogen peroxide, even when incubated with a protease over several hours.

Practical Procedure for GEOx Immobilization of Enzyme on Substrate
For each kilogram of Silica gel:
In 1.5 liters of DI water, dissolve the following:
   3.24 g Sodium Phosphate monobasic
   40 g Sodium Bicarbonate
   20 g Sodium Chloride
Adjust the pH to 5.6 with Sodium Hydroxide or Hydrochloric Acid (or Phosphoric Acid). After solution in clear, filter through a low pore size filter.
Add about 1200000 units of Glucose Oxidase (check the activity of Glucose Oxidase before starting a batch). Mix (with heat if necessary—do not exceed 40° C.), Solution should be clear yellow-green (the color depends on the source of enzyme).
Add the solution on the Silica. Mix until homogenous with mild agitation. Dry in air current. Do not exceed 40° C.

Preparation of Immobilized Glucose Oxidase Enzyme with Diatomaceous Earth Procedure:
Celite R-685
   One container Celite/liter cone HCL
   Solution should sit overnight
   The material is then exhaustively washed (12-15x) with D.1 water in fritted glass filter—Wash until 0 conductivity (35-45 uv)
   Material referred to as AWM
Silanization
   Prepare a 10% Soln of Silane (40 ml Silane q.s to 400 ml with distilled water)
   Adjust pH to 3.0 with 6 M HCL
   Add Silane Soln to AWM (1:2) (200 g in 400 ml)

Place mixture in water bath at 75° C. for 4 hrs
Mixture is then filtered
Mixture is then referred to as AWM-S
Place AWM-S in oven and heat at 115° C. until completely dry (10-12 hrs)

Gluteraldehyde
Prepare a 2.5% solo of Gluteraldehyde (take 250 ml of 25% soln qs to 2500 ml)—Take the 2.5 liters of soln and add to 100 g of AWM-S(Ratio 25:1)
Adjust pH to 7.0 with NaOH
Place soln on stir plate for 60 mins
Filter soln and refer to as AWM-S-A
Wash 3 times with distilled water and then once with 0.05M Na2PO4 buffer (0.05 M $Na_2PO_4$=0.71 g/L)
Dry overnight Glucose Oxidase G.O
Take 50,000 units of G.O and q.s in volumetric flask to 100 ml with 0.05 M buffer
Take 100 ml of the GO soln and add 25 g of AWM-S-A—Stir for 4 hours
Filter and wash sol with distilled water—G.O/Base is then stored in the fridge Testing Procedure for Immobilized Glucose Oxidase Activity Reagents
1. Potassium phosphate buffer 0.01 M with Sodium Acetate buffer 0.01 M at pH=5.6.
2. 2. Glucose Oxidase (several consecutive dilutions) in buffer.
3. D-Glucose 10% in buffer.
4. o-Dianisidine 1ICI 0.1 M in buffer.
5. Peroxidase solution 6 purpurogallin units/mL in DI water.
6. Immobilized glucose oxidase (on silica powder). (minimum 800 International enzyme units per gram of immobilized enzyme)

Procedure
For Standard Curve:
Make consecutive dilutions of glucose oxidase in buffer (5.7, 10, 12, 15 units/mL). In each test tube add:
1 mL glucose oxidase solution
1 mL o-Dianisidine
1 mL D-Glucose
1 mL peroxidase solution.
Measure and record absorbance at 436 am for 10 minutes, using a mixture of 1 mL o-Dianisidine. 1 mL D-glucose, 1 mL peroxidase solution, 1 mL phosphate buffer as blank. Plot rate of absorbance vs. concentration. Calculate the slope.
FOR IMMOBILIZED GLUCOSE OXIDASE: (identified as $GEO_x$ herein) Assign potency to the immobilized glucose oxidase.
In 8 test tubes add the following reagents:
0.1 g immobilized glucose oxidase
5 mL phosphate buffer.
Put the test tubes on a stirring plate in a temperature bath at 30° C. Mark the test tubes for each time point. Time points: 10 minutes. 30 minutes-60 minutes, 2 hours, 4 hours, 8 hours, 12 hours, 24 hours.

Commercial toothpaste is removed from its container and a predetermined amount of thusly prepared immobilized glucose oxidase is added to the toothpaste with thorough mixing. No special preparation is needed, as the immobilized glucose oxidase is insoluble and will disperse throughout the product.

Immobilized glucose oxidase can be added to a dry mix tablet, such as lozenge, for application to the oral cavity.

Immobilized glucose oxidase of this invention can be added to chewing gum mix without additional preparation.

Alternatively, glucose oxidase can be coated with polyethylene glycol and incorporated into a mouthwash to form a clear solution. In this manner, it is protected from protease attack, while facilitating glucose conversion.

Formulation Example I for an Acne Treatment Lotion

| Acne stick Formula GEOx Acne Stick | |
|---|---|
| Ingredient | % |
| Octyl Dodecanol | 5.0 |
| C12-15 Alkyl Benzoate | 28.0 |
| N-Acyl Amino Acid Amide | 2.0 |
| Amine-Terminated Polyamide | 40.0 |
| Phenyl Dimethicone | 4.0 |
| Isohexadecane | 15.0 |
| Salicylic Acid | 2.0 |
| $GEO_x$ Powder | 4.0 |

| Lip Gloss Formula | |
|---|---|
| Ingredient | % |
| Octyl Dodecanol | 5.0 |
| Polybutene | 62.0 |
| Mineral Oil | 18.0 |
| Flavoring Agents | 1.0 |
| Pigments | 10.0 |
| GEOx | 4.0 |

Procedure: Pre-mix Octyl Dodecanol, Polybutene and Mineral Oil; mix until uniform. Add pigments and mill until color is developed; add Spearmint (Flavoring Agent) and mix until uniform. Add GEOx and mix until uniform.

Medical Coating for Catheter or Implantable Device
A coating solution is prepared having the following formulation

| Component | Supplier/Designtion | (%) |
|---|---|---|
| Urethane | Permuthane/UE41-222 (at 20% solids) | 66.70 |
| Polyvinylpyrrolidone copolymer | GAF/ACP 1030 (postneutralized) | 13.30 |
| $GEO_x$ | | 3% |
| Aziridine | Permuthane1KM10-1703 | 4.80 |
| Distilled water | | 15.20 |

| Formulation of quick dissolving films | |
|---|---|
| Composition: coating solution | Ex. |
| Pullalan (P-20) w % | 17.5 |
| PVA (Vinol 125) w/w % | |
| Acylsulfame K w % | |
| Peppermint w % | 1.0 |
| Cooling Flavor | 2 |
| Citric acid w % | 0.8 |
| Cremphor EL40 w % A | 1.0 |
| Benzoic acid | 0.1 |
| FD & C blue #1 w | |
| FD & C yellow #5 | |
| Ethanol w/w % | 10.6 |

-continued

| Formulation of quick dissolving films | |
|---|---|
| Composition: coating solution | Ex. |
| GEO$_x$ F M | 10% |
| Water w % | 55.025 |

Example 6

Whitening Solution

Mix the Glycol and PAOPA while heating to 60 C. When the mixture is clear, add sucrolose and cool to room temperature before mixing remaining ingredients.

| | |
|---|---|
| USP H2O2 | 6% |
| Gantrez S97-BF maleic anhydride/vinylpyrolidone (ISP) | 3% |
| Spearmint Oil | 5% |
| Flavor | .5% |
| Sucralose (McNeil) | .5% |
| GEOx | 5% |
| Sylvagel 6100 (Arizona Chemical-polyamide polyether) | 2% |
| USP 1-3 Butylene Glycol | 87.5% |

Place in appropriate dispensing package like a twist pen or crushable ampoule.

Activity Example I

Determination of Halitosis Pre- and
Post-Application of GEOx Lip Gloss

Objective

The purpose of this comparison study is to determine the efficacy of a test product designed to improve breath odor.

Subjects

Seventeen healthy males and females aged 18 years and older participated in this study. All subjects have regular dental care and did not have an active diagnosis of halitosis. All subjects reviewed and stared medical histories and informed consent statements. These remain on file at Co-inventor Peter T. Pugliese, M.D. & Associates.

Procedure

All subjects enrolled in this study reviewed and signed an informed consent statement prior to any study procedures being performed. Briefly, subjects were not to eat, drink or smoke for at least two hours prior to this study.

Breath odor was tested on an RH-17 Series Haliometer (Interscan Corporation, Chatsworth, Calif. 91313)—an instrument designed to measure volatile sulfur compounds. First, a drinking straw was inserted into the connector of the sampling rube: The other end of the straw was placed on the back of the tongue. The instrument's pump draws the oral breath samples in at a set flow rate.

The instrument had a zero reading of 10 ppb before breath samples were collected. Next, the instrument is set to Sample to begin taking breath measurements. The instrument automatically collected three sets of breath samples for 30 seconds each. The average reading result is noted. The subjects applied the GEOx Lip Gloss to the upper and lower lips. Immediately after application of the GEOx Lip Gloss, subjects licked their lips. After 45 minutes, three post-application breath samples were collected and the average reading result is noted. During the test, the flow indicator was monitored to ensure that the subject had the straw in the correct position to avoid erroneous readings. The duration of this study was approximately one hour.

Results and Conclusions

Based on the data obtained in this study on 17 subjects, the following conclusions may be made: 1. Pre-application average breath readings of volatile sulfur compounds was 41.65 2. Post-application average breath readings of volatile sulfur compounds was 24.59. 3. Fourteen out of 17 subjects had a decrease in volatile sulfur compounds after one application of GEOx Lip Gloss.
4. Average percent reduction of volatile sulfur compounds after one application of GEOx Lip Gloss was 40.96%.

Activity Example II

Determination of Halitosis Pre- and
Post-Application of GEOx Breath Strip

Objective

The purpose of this comparison study was to determine the efficacy of a test product designed to improve breath odor.

Subjects

Fifteen healthy males and females aged 18 years and older participated in this study. All subjects have regular dental care and did not have an active diagnosis of halitosis. All subjects reviewed and signed medical histories and informed consent statements. These remain on file at Co-inventor Peter T. Pugliese, M.D. & Associates.

Procedure

All subjects enrolled in this study reviewed and signed an informed consent statement prior to any study procedures being performed. Briefly, subjects were not to eat, drink or smoke for at least two hours prior to this study.

Breath odor was tested on an RH-I7 Series Haliometer (Interscan Socproation, Chatsworth. Calif. 91313)—an instrument designed to measure volatile sulfur compounds. First, a drinking straw was inserted into the connector of the sampling tube. The other end of the straw was placed on the back of the tongue. The instruments pump draws the oral breath samples in at a set flow rate.

The instrument had a zero reading of +10 ppb before breath samples were collected. Next, the instrument is set to Sample to begin taking breath measurements. The instrument automatically collected three sets of breath samples for 30 seconds each. The average reading result is noted. The subjects applied the GEOx Breath Strip on the center of the tongue. Immediately after application of the GEOx Lip Breath Strip, subjects closed their mouth. After 10, 30, 60, 120 and 180 minutes, three post-application breath samples were collected and the average reading result is noted. During the test, the flow indicator was monitored to ensure that the subject had the straw in the correct position to avoid erroneous readings. The duration of this study was approximately 3.5 hours.

Results and Conclusions

Based on the data obtained in this study on 15 subjects, the following conclusions may be made: 1. The pre-application (baseline) average breath readings of volatile sulfur compounds was 53.13 2. Post-application average breath readings of volatile sulfur compounds was:

| Time (minutes) | Reading (ppb) |
|---|---|
| 0 | 21.33 |
| 10 | 7.13 |
| 30 | 19.60 |
| 60 | 39.33 |
| 120 | 38.75 |
| 180 | 46.27 |

3. All subjects had a decrease in volatile sulfur compounds after one application of GEOx Breath Strip.
4. Average percent reductions of volatile sulfur compounds after one application of GEOx Breath Strip were:

| Time (minutes) | % |
|---|---|
| 0 | 59.85 |
| 10 | 86.58 |
| 30 | 63.11 |
| 60 | 25.97 |
| 120 | 27.07 |
| 180 | 12.91 |

5. We conclude the GEOx Breath Strip is an effective way to reduce halitosis.

Activity Example III

Results of Microinhibition Study Comparing GEOx. To Glucose Oxidase Using Zone of Inhibition Assay OBJECTIVE: To determine if GEOx, has the ability to reduce the proliferation of bacteria as well as Glucose oxidase.
MATERIALS: (1) *Escherichia coli* ATCC #8739, (2) *Staphyococcus aureus* ATCC #6538, (3) *Psudeoomonas aeruginosa* ATTC #9027, (4) Nutrient agar plates (15× 100 mm) containing 5% glucose, (5) Pennicylinders sterile, (6) Sterile deonized water, (7) Incubator 35-37 C, (8) Pipettes (sterile, disposible), (9) Bent glass rod, sterile, (10) Digital calipers, (11) GEOx. Lot # JGeO, and BioCat Glucose oxidase, Lot # Gois-Z028.
PROCEDURE: Each bacteria is grown in individual tubes for approximately 24 hours ~a 36 C in 10 ml. nutrient broth. 0.1 ml of this inoculum is swabbed onto agar plates using rapid back-and-forth strokes while turning the plate to cover the agar surface evenly. Sterile pennicylinders are strategically placed onto the agar.
Each plate is labeled for GEOx, sample is being tested. 0.25 grams of the GEOx (1000 units/g), samples are put into pennicylinders, followed by 0.13 grams of sterile deionized water. Like procedure is followed with glucose oxidase sample as an antimicrobial control (15000 units/g) vs. GEOx. The plates are incubated for 24 hours. Zones are measured in millimeters with digital calipers.

| RESULTS: | E. Coli | Staphylococcus | Pseudon |
|---|---|---|---|
| GEOx, | 10.67 mm | 6.91 mm | 7. mm |
| Glucose Oxidase | 12.26 mm | 11.86 mm | 9.42 mm |
| GEOx/Glucose Oxidase, Difference in Degree Of Inhibition | 12.9% | 41% | 22.7% |

The presence of a zone indicates antimicrobial activity. Therefore, based on these results, the GEOx, of the invention has bacteriocidal properties even at a significantly lower concentration of units of active enzyme/g vs untreated enzyme.

We claim:
1. A method for continuously generating hydrogen peroxide in a protease-containing environment, the method comprising:
(a) sequestering, without chemical immobilization, an enzyme capable of continuously generating hydrogen peroxide in the presence of reactant substrate in a protease-containing environment within the pores of a three-dimensional porous matrix comprising silica, silica gel, diatomaceous earth, polyacrylate, clay, silanized diatomaceous earth or fumed glass microbeads, wherein the pore size of the matrix has a diameter between 300 and 800 Angstroms, wherein said porous matrix protects said enzyme from proteolysis, the sequestering comprising:
(i) contacting a 3-dimensional porous matrix comprising silica, silica gel, diatomaceous earth, polyacrylate, clay, silanized diatomaceous earth or fumed glass microbeads with buffered deionized water to provide a pre-conditioned matrix;
(ii) contacting a buffered solution of said enzyme with the pre-conditioned matrix to obtain an enzyme-containing matrix; followed by:
(iia) drying the enzyme-containing matrix; or
(iib) rinsing the enzyme-containing matrix with an saline solution, buffer and deionized water,
to obtain a three-dimensional porous matrix containing a sequestered enzyme that is capable of continuously generating hydrogen peroxide in the presence of reactant substrate wherein said porous matrix excludes bulkier enzymes but allows for the transport of the reactant substrate though said porous matrix and for diffusion of hydrogen peroxide out of said porous matrix at a steady state;
(b) contacting the resultant enzyme-containing porous matrix from step (a) with a protease-containing environment that contains a reactant substrate for the enzyme, wherein the protease-containing environment is a body cavity or a bodily fluid of a mammal; and
(c) generating hydrogen peroxide at steady state in said protease-containing environment.
2. The method of claim 1, wherein said enzyme capable of continuously generating hydrogen peroxide in the presence of reactant substrate is selected from the group consisting of: glucose oxidase; lipo-oxidase; amine oxidase; and diamine oxidase.
3. The method of claim 2, where the enzyme capable of continuously generating hydrogen peroxide in the presence of reactant substrate is glucose oxidase.
4. The method of claim 3, wherein said porous matrix is silica gel and wherein said diameter of said pores is not more than about 350 angstroms.
5. The method of claim 3, wherein said porous matrix comprises diatomaceous earth and the diameter of said pores is not more than about 800 angstroms.
6. The method of claim 1, wherein said protease containing environment comprises the oral cavity of a mammal, the enzyme is glucose oxidase and glucose is present in said oral cavity.

* * * * *